United States Patent
Sako

(10) Patent No.: US 9,778,214 B2
(45) Date of Patent: Oct. 3, 2017

(54) X-RAY ANALYZING APPARATUS

(71) Applicant: RIGAKU CORPORATION, Tokyo (JP)

(72) Inventor: Yukio Sako, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 15/458,326

(22) Filed: Mar. 14, 2017

(65) Prior Publication Data
US 2017/0184519 A1 Jun. 29, 2017

Related U.S. Application Data

(63) Continuation of application No. PCT/JP2015/074270, filed on Aug. 27, 2015.

(30) Foreign Application Priority Data

Sep. 18, 2014 (JP) .................................. 2014-190249

(51) Int. Cl.
*G01N 23/223* (2006.01)
*G01T 1/17* (2006.01)

(52) U.S. Cl.
CPC .............. *G01N 23/223* (2013.01); *G01T 1/17* (2013.01); *G01N 2223/076* (2013.01); *G01N 2223/303* (2013.01)

(58) Field of Classification Search
CPC .. G01T 1/17; G01T 1/16; G01T 1/247; G01T 1/36; G01T 1/40; G01T 7/00;
(Continued)

(56) References Cited

U.S. PATENT DOCUMENTS 5,200,625 A 4/1993 Kawai
5,357,551 A 10/1994 Bolk et al.
(Continued)

FOREIGN PATENT DOCUMENTS

CN 1064549 A 9/1992
CN 102933982 A 2/2013
(Continued)

OTHER PUBLICATIONS

International Preliminary Report on Patentability and Translation of the Written Opinion, dated Mar. 30, 2017, from the International Bureau in counterpart International application No. PCT/JP2015/074270.
(Continued)

*Primary Examiner* — Glen Kao
(74) *Attorney, Agent, or Firm* — Sughrue Mion, PLLC

(57) ABSTRACT

The X-ray analyzing apparatus according to the present invention includes, in combination: a first correcting unit (13A, 13B) to output a first gain to cause a pulse height of a target peak which is estimated on the basis of a sum of counting rates obtained in preliminary measurement, to match a predetermined expected pulse height; and a second correcting unit (14A, 14B) to output, in real time through feedback control, a second gain to be added to the first gain in order to cause the pulse height of the target peak detected within a predetermined energy range, to match the expected pulse height, and further includes a feedback control stopping unit (16A, 16B) to appropriately determine presence/absence of an interfering line with respect to the target peak, and to set, when determining that the interfering line exists, the gain to a fixed value including only the first gain.

4 Claims, 3 Drawing Sheets

(58) Field of Classification Search
CPC ......... G01N 2223/304; G01N 2223/50; G01N 23/223; G01N 2223/076; G01N 2223/303
See application file for complete search history.

(56) References Cited

U.S. PATENT DOCUMENTS

| | | | |
|---|---|---|---|
| 8,374,814 B2 | 2/2013 | Sako | |
| 2012/0207277 A1* | 8/2012 | Sako | ........................ G01T 1/17 378/91 |
| 2014/0284478 A1* | 9/2014 | Sako | ........................ G01T 1/16 250/336.1 |

FOREIGN PATENT DOCUMENTS

| | | |
|---|---|---|
| JP | 58-187885 A | 11/1983 |
| JP | 62-12475 B2 | 3/1987 |
| JP | 6-130155 A | 5/1994 |
| JP | 10-318946 A | 4/1998 |
| JP | 2005-9861 A | 1/2005 |
| JP | 2005-291961 A | 10/2005 |

OTHER PUBLICATIONS

International Search Report of PCT/JP2015/074270 dated, Nov. 24, 2015 (PCT/ISA/210).
Decision to Grant issued Jul. 12, 2016 on Corresponding Japanese Patent Application No. 2014-140249 dated Jul. 12, 2016.
Communication dated Aug. 3, 2017, from the State Intellectual Property Office of People's Republic of China in counterpart Application No. 201580049565.1.

* cited by examiner

X-RAY ANALYZING APPARATUS

CROSS REFERENCE TO THE RELATED APPLICATION

This application is a continuation application, under 35 U.S.C. §111(a), of international application No. PCT/JP2015/074270, filed Aug. 27, 2015, which claims priority to Japanese patent application No. 2014-190249, filed Sep. 18, 2014, the entire disclosure of which is herein incorporated by reference as a part of this application.

BACKGROUND OF THE INVENTION

Field of the Invention

The present invention relates to an X-ray analyzing apparatus which corrects so-called peak shift.

Description of Related Art

In a conventional wavelength dispersive X-ray fluorescence spectrometer, a sample is irradiated with primary X-rays, a spectroscopic device monochromates fluorescent X-rays generated from the sample, a detector detects the monochromated fluorescent X-rays to generate pulses. A voltage of the pulse, that is, a pulse height corresponds to energy of the fluorescent X-rays, and specifically, is considered to be proportional to the energy. The number of pulses per unit time corresponds to intensity of the fluorescent X-rays. Thus, among the pulses, pulses in a predetermined voltage range (defined by an upper limit value and a lower limit value, and called "window") are selected by a pulse height analyzer, and a counting rate (number of pulses per unit time) of the pulses is obtained, as an X-ray intensity, by a counting unit such as a scaler.

However, it has been known that, for example, in a case where a proportional counter is used as the detector, when high-intensity fluorescent X-rays are incident on the detector, a pulse voltage, that is, a pulse height to be sent to the pulse height analyzer may be suddenly lowered by several tens percent in a several seconds, and further, may be unstable within a range of approximately several percent for next ten and several minutes. This phenomenon is called peak shift, pulse height drift, or the like. When peak shift occurs, measurement is performed using an inappropriately set window which is shifted from a target wavelength, and thus, accurate analysis is impossible (see Patent Documents 1 to 4). This problem may also occur in X-ray analyzing apparatuses other than wavelength dispersive X-ray fluorescence spectrometers, and may also occur, which varies in degree, when detectors other than proportional counters are used (see Patent Documents 3 and 4).

Accordingly, as a first conventional technology for correcting peak shift, there is an apparatus that estimates a peak position (a pulse height of a target peak which is an upward projected peak in an X-ray energy spectrum to be analyzed, and more specifically, a pulse height at a vertex of the target peak) on the basis of an X-ray intensity obtained in preliminary measurement, and that changes, in main measurement, a gain of pulses from the detector such that the estimated peak position matches a reference position (an expected pulse height) corresponding to an original pulse height (see Patent Documents 1 and 2). Here, a relationship between the X-ray intensity and a lowered and stabilized peak position in the energy spectrum is obtained in advance through an experiment. In addition, as a second conventional technology for correcting peak shift, there is an apparatus that detects the peak position within a predetermined energy range including the reference position, and that dynamically (in real time) changes the gain of pulses from the detector such that the detected peak position matches the reference position (see Patent Documents 3 and 4).

RELATED DOCUMENT

Patent Document

[Patent Document 1] JP Laid-open Patent Publication No. S58-187885

[Patent Document 2] JP Laid-open Patent Publication No. 2005-9861

[Patent Document 3] JP Laid-open Patent Publication No. H06-130155

[Patent Document 4] JP Examined Patent Publication No. S62-12475

However, at least several seconds are required to stabilize the peak position which is lowered by peak shift. Thus, when the first conventional technology is used before the peak position is stabilized, to estimate the peak position, correct the peak position by changing the gain, and start the main measurement, the corrected peak position is higher than the reference position corresponding to the original pulse height until the lowered peak position becomes stable. This makes accurate analysis impossible. However, when, in order to perform accurate analysis, start of the main measurement is delayed until the peak position which is lowered by peak shift becomes stable, at least several seconds needs to be waited. A time taken for the analysis is accordingly longer. In a case where a pulse height is unstable for ten and several minutes after being suddenly lowered, performing accurate analysis in a short time is more difficult. In addition, the relationship between the X-ray intensity and the lowered and stabilized peak position in the energy spectrum is slightly different among X-ray analyzing apparatuses. Thus, in order to perform accurate analysis, such a relationship needs to be obtained in advance through an experiment for each X-ray analyzing apparatus. In each of the X-ray analyzing apparatuses, when a detector is exchanged, the relationship needs to be obtained for the detector after exchange.

On the other hand, in the second conventional technology, when an X-ray intensity suddenly changes, or an interfering line (for example, a secondary or higher order reflection line for X-rays to be analyzed) is included in an energy spectrum, the peak position may be incorrectly detected. In this case, accurate analysis is impossible.

SUMMARY OF THE INVENTION

Therefore, an object of the present invention is to provide an X-ray analyzing apparatus capable of correcting, even when peak shift occurs, the peak shift speedily and appropriately, and performing accurate analysis in a short time.

In order to achieve the above object, the present invention is an X-ray analyzing apparatus that includes: a detector configured to generate a number of pulses having pulse heights corresponding to energy of incident X-rays, the number corresponding to intensity of the X-rays; a high-speed AD converter configured to digitalize the pulses generated by the detector; a pulse height stabilizer configured to stabilize, for pulses inputted from the high-speed AD converter, a pulse height of a target peak which is a peak in an X-ray energy spectrum to be analyzed; and a counting unit configured to obtain, for pulses from the pulse height stabilizer, a counting rate within a set pulse height range.

The pulse height stabilizer includes: an input pulse multiplier configured to multiply pulses inputted from the high-speed AD converter with an inputted gain, and to output the pulses; a first correcting unit configured to, in preliminary measurement before main measurement, obtain, for pulses from the input pulse multiplier, a sum of counting rates, to estimate the pulse height of the target peak on the basis of the obtained sum of counting rates, and to output a first gain which is a gain to cause the estimated pulse height of the target peak to match a predetermined expected pulse height; a second correcting unit configured to detect the pulse height of the target peak within a predetermined energy range including the expected pulse height on the basis of pulses from the input pulse multiplier, and to output, in real time through feedback control, a second gain which is a gain to be added to the first gain in order to cause the detected pulse height of the target peak to match the expected pulse height; a gain adder configured to add the inputted first gain to the inputted second gain to obtain a gain, and to output the gain to the input pulse multiplier; and a feedback control stopping unit configured to determine presence/absence of an interfering line with respect to the target peak, and, when determining that the interfering line exists, to stop the second correcting unit outputting the second gain, thereby to set the gain to be inputted to the input pulse multiplier, to a fixed value including only the first gain.

According to the present invention, the first correcting unit configured to output the first gain to cause the pulse height of the target peak which is estimated on the basis of the sum of counting rates obtained in the preliminary measurement, to match the predetermined expected pulse height, and the second correcting unit configured to output, in real time through feedback control, the second gain to be added to the first gain in order to cause the pulse height of the target peak detected within the predetermined energy range, to match the expected pulse height are provided in combination. Therefore, even when peak shift occurs, in a considerably short time, the first gain is outputted as a gain initial value and the second gain is added to the first gain so that feedback correction is performed. Therefore, start of the main measurement does not need to be waited until the pulse height of the target peak which is lowered by peak shift becomes stable. Further, even when the X-ray intensity suddenly changes, the pulse height of the target peak is not lost but can be correctly detected. Moreover, the feedback control stopping unit is provided which is configured to determine presence/absence of the interfering line with respect to the target peak, and to set, when determining that the interfering line exists, the gain to the fixed value including only the first gain. Accordingly, even in a situation where the interfering line is mixed in the energy spectrum and the second correcting unit is unable to correctly detect the pulse height of the target peak, the appropriately estimated pulse height of the target peak is caused to match the expected pulse height and is stabilized, by using the first gain outputted from the first correcting unit. Therefore, even when peak shift occurs, the peak shift can be corrected speedily and appropriately, so that accurate analysis can be performed in a short time.

In the present invention, preferably, in the second correcting unit, the predetermined energy range is a range from a low pulse height threshold which is lower than the expected pulse height by a half to two times of a half value width of the target peak, to a first high pulse height threshold which is higher than the expected pulse height, and the low pulse height threshold and the first high pulse height threshold are set such that, for the X-ray energy spectrum to be analyzed, a total counting rate within a range from the low pulse height threshold to the expected pulse height is equal to a total counting rate within a range from the expected pulse height to the first high pulse height threshold; and for pulses from the input pulse multiplier, an average pulse height obtained by averaging pulse heights within the range from the low pulse height threshold to the first high pulse height threshold is detected as the pulse height of the target peak.

Further, preferably, in the feedback control stopping unit, the low pulse height threshold and a second pulse height threshold, which is equal to or greater than two times of the expected pulse height are set, and in the preliminary measurement, for pulses from the input pulse multiplier, when a difference between the pulse height of the target peak detected by the second correcting unit and an average pulse height obtained by averaging pulse heights within a range from the low pulse height threshold to the second high pulse height threshold is greater than a predetermined value, it is determined that the interfering line exists. In this case, presence/absence of the interfering line with respect to the target peak can be determined sufficiently appropriately.

In the present invention, it is also preferable that, in the preliminary measurement, when a value obtained by adding the first gain to the second gain is outside a predetermined range, the feedback control stopping unit determines that the interfering line exists. Also in this case, presence/absence of the interfering line with respect to the target peak can be determined sufficiently appropriately.

In the present invention, after a predetermined waiting time corresponding to the sum of counting rates obtained by the first correcting unit has elapsed since the feedback control stopping unit determines in the preliminary measurement that the interfering line exists, the feedback control stopping unit may set a gain to be inputted to the input pulse multiplier, to the fixed value including only the first gain, and the main measurement may be started. As described above, in order to perform accurate analysis in the main measurement using only the first gain, start of the main measurement is desired to be delayed until the pulse height of the target peak which is lowered by peak shift becomes stable. However, whether or not a waiting time for this is necessary is determined depending on accuracy desired for analysis and a time which can be taken for the analysis. Moreover, the length of the waiting time should be set appropriately depending on the sum of counting rates obtained by the first correcting unit.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
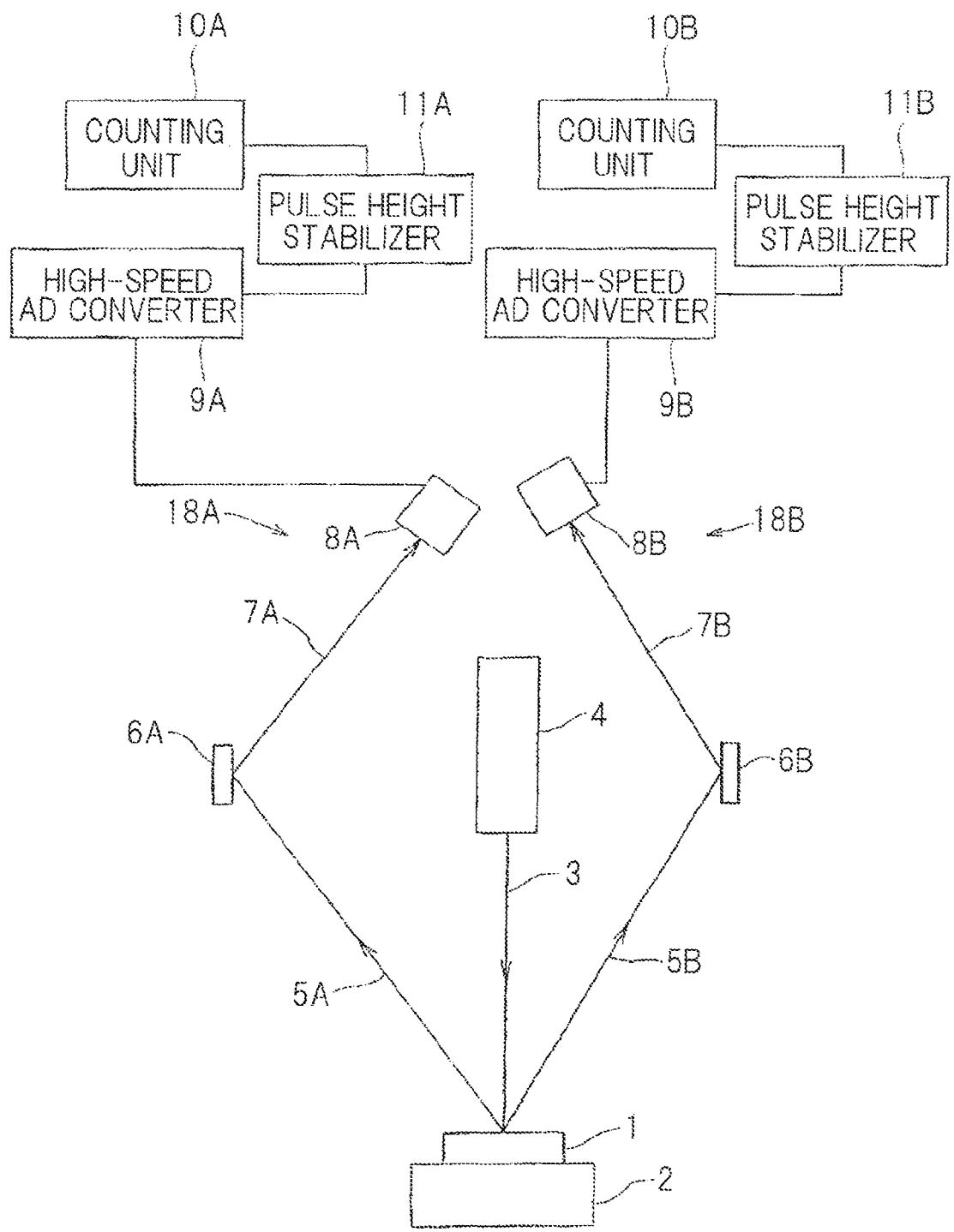
FIG. 1 schematically illustrates a wavelength dispersive X-ray fluorescence spectrometer according to an embodiment of the present invention.

Hereinafter, a wavelength dispersive X-ray fluorescence spectrometer according to an embodiment of the present invention will be described with reference to the drawings. As illustrated in FIG. 1, the spectrometer includes detection units 18A, 18B provided for the respective wavelengths of secondary X-rays 7A, 7B such as fluorescent X-rays to be measured. The detection units 18A, 18B include spectroscopic devices 6A, 6B, detectors 8A, 8B, high-speed AD converters 9A, 9B, pulse height stabilizers 11A, 11B, and counting units 10A, 10B, respectively. This X-ray fluorescence spectrometer is a wavelength dispersive type and a simultaneous multi-elements analysis type. Preamplifiers may be provided between the detectors 8A, 8B and the high-speed AD converters 9A, 9B, respectively.

More specifically, the spectrometer includes: a sample table 2 on which a sample 1 is placed; an X-ray source 4 which is an X-ray tube configured to irradiate the sample 1 with primary X-rays 3; the spectroscopic devices 6A, 6B, each of which is configured to monochromate secondary X-rays 5A, 5B such as fluorescent X-rays generated from the sample 1; the detectors 8A, 8B which are gas-flow type proportional counters, on each of which the secondary X-rays 7A, 7B monochromated by the spectroscopic device 6A, 6B are incident, and each of which generates a number of pulses having pulse heights corresponding to energy of the X-rays 7A, 7B, the number corresponding to intensity of the X-rays 7A, 7B; and high-speed AD converters 9A, 9B, each of which is configured to digitalize the pulses generated by the detector 8A, 8B.

The spectrometer further includes: the pulse height stabilizers 11A, 11B, each of which is configured to stabilize, for pulses inputted from the high-speed AD converter 9A, 9B, a pulse height (represented by a pulse height at a vertex of an upward projected target peak) of a target peak which is a peak in an X-ray energy spectrum to be analyzed; and the counting units 10A, 10B, each of which is configured to obtain, for pulses from the pulse height stabilizer 11A, 11B, a counting rate within a set pulse height range. Specifically, each of the counting units 10A, 10B is a pulse height analyzer in which a single pulse height range is set, or a multichannel pulse height analyzer in which multiple continuous pulse height ranges are set to obtain a counting rate for each pulse height range.

Figure 2:
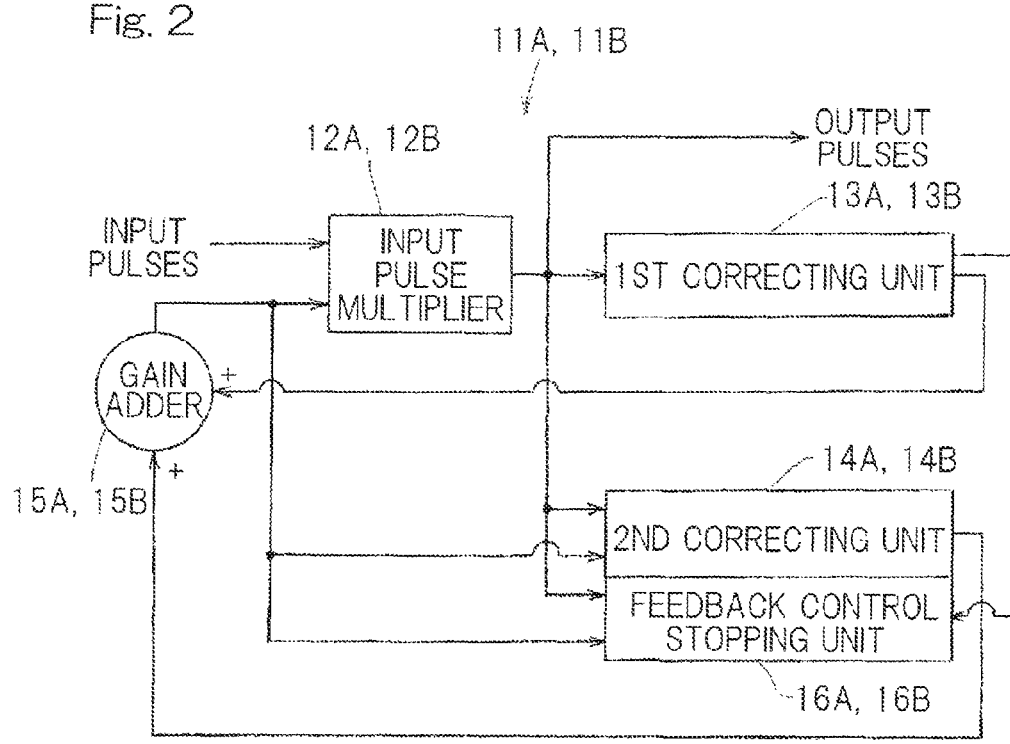
FIG. 2 is a block diagram illustrating a pulse height stabilizer of the spectrometer.

In the case of the pulse height stabilizer 11A corresponding to the secondary X-rays 7A, as an example, the pulse height stabilizer 11A includes an input pulse multiplier 12A, a first correcting unit 13A, a second correcting unit 14A, a gain adder 15A, and a feedback control stopping unit 16A, as illustrated in FIG. 2. The input pulse multiplier 12A multiplies the pulses inputted from the high-speed AD converter 9A (referred to as "input pulses" for simplicity in FIG. 2, and may be referred as the same also in the following description) by an inputted gain, and outputs the resultant pulses.

In preliminary measurement before main measurement, the first correcting unit 13A obtains a sum of counting rates for pulses inputted from the input pulse multiplier 12A, estimates the pulse height of the target peak on the basis of the obtained sum of counting rates, and outputs a first gain which is a gain to cause the estimated pulse height of the target peak to match a predetermined expected pulse height. The first gain can vary from 1.0 to 2.0, for example. The predetermined expected pulse height is an original pulse height in a case where peak shift does not occur, and is 200 mV, for example.

Regarding peak shift, a relationship between the sum of counting rates (corresponding to a sum of intensities of X-rays within a wavelength region detected by the detector) of the input pulses and a lowered and stabilized pulse height of the target peak in the energy spectrum is obtained in advance through an experiment, and the relationship is stored in the first correcting unit 13A. Thus, the first correcting unit 13A can estimate the pulse height of the target peak on the basis of the sum of counting rates obtained in the preliminary measurement before the main measurement, and outputs the first gain which is the gain to cause the estimated pulse height of the target peak to match the expected pulse height. The first gain can be used as an initial value of the gain to be multiplied to the input pulse. Here, in the present invention, a second gain (described later) is added to the first gain to perform correction by feedback. Thus, accurate analysis is possible even when the relationship between the sum of counting rates and the pulse height of the target peak is not strictly obtained for each X-ray analyzing apparatus or each detector.

The second correcting unit 14A detects the pulse height of the target peak within a predetermined energy range including the expected pulse height on the basis of the pulses from the input pulse multiplier 12A, and outputs, in real time through feedback control, a second gain which is a gain to be added to the first gain in order to cause the detected pulse height of the target peak to match the expected pulse height. The gain adder 15A adds the inputted first gain to the inputted second gain to obtain a gain, and outputs the gain to the input pulse multiplier 12A.

A detailed description is given of setting of the predetermined energy range including the expected pulse height and detecting operation of the pulse height of the target peak in the second correcting unit 14A. In the second correcting unit 14A included in the X-ray analyzing apparatus according to the present embodiment, the predetermined energy range is a range from a low pulse height threshold which is lower than the expected pulse height by a half to two times of a half value width of the target peak, to a first high pulse height threshold which is higher than the expected pulse height. Here, for the X-ray energy spectrum to be analyzed, the low pulse height threshold and the first high pulse height threshold are set, through an experiment performed in advance, such that a total counting rate in a range from the low pulse height threshold to the expected pulse height is equal to a total counting rate in a range from the expected pulse height to the first high pulse height threshold. In addition, for the pulses from the input pulse multiplier 12A, the second correcting unit 14A detects, as the pulse height of the target peak, an average pulse height which is obtained by averaging, by an exponential smoothing method, pulse heights within the range from the low pulse height threshold to the first high pulse height threshold. To obtain the average pulse height in the present invention, in addition to the exponential smoothing method (exponential moving average method), a simple moving average method, a weighted moving average method, or the like may be used.

For example, the feedback control stopping unit 16A is coupled and integrated with the second correcting unit 14A to be able to transmit/receive a signal to/from each other. The feedback control stopping unit 16A determines presence/absence of an interfering line with respect to the target peak. When determining that the interfering line exists, the feedback control stopping unit 16A stops the second correcting unit 14A outputting the second gain, thereby sets the gain to be inputted to the input pulse multiplier 12A, to a fixed value (value not varying with time) including only the first gain.

A detailed description is given of criteria for the feedback control stopping unit 16A to determine presence/absence of the interfering line. In the feedback control stopping unit 16A included in the X-ray analyzing apparatus according to the present embodiment, the low pulse height threshold and a second high pulse height threshold which is equal to or greater than two times of the expected pulse height are set. In the preliminary measurement, for the pulses from the input pulse multiplier 12A, when a difference between the pulse height of the target peak detected by the second correcting unit 14A as described above and an average pulse height value obtained by averaging, by the exponential smoothing method, pulse heights within a range from the low pulse height threshold to the second high pulse height threshold is greater than a predetermined value, it is determined that the interfering line exists. This is referred to as a first determination criterion.

Figure 3:
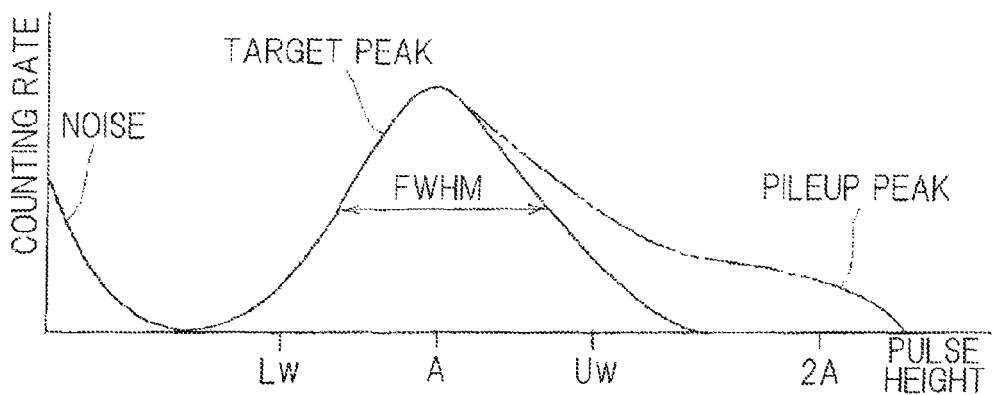
FIG. 3 illustrates examples of energy spectrums including their respective target peaks.

Adequacy for configuring the second correcting unit 14A and the feedback control stopping unit 16A as described above is described. FIG. 3 shows examples of the energy spectrums including their respective target peaks, in each of which the half value width FWHM of the target peak is relatively wide and no escape peak or no interfering line exists. As the X-ray intensity increases (counting rate becomes greater), the target peak is deformed more so as to have a long skirt at the high pulse height side. As the X-ray intensity further increases, a so-called pileup peak appears at a pulse height which is two times of the pulse height of the target peak, as indicated by a two-dot chain line. The energy spectrum in which no pileup peak appears is indicated by a solid line, and the energy spectrum in which a pileup peak appears is indicated by the two-dot chain line. The two energy spectrums are normalized with the pulse heights and the counting rates at the vertexes of the target peaks, respectively, and shown in an overlapping manner (the same applies for FIG. 4).

To accurately detect the pulse height of the target peak in each of those energy spectrums, it is appropriate to set the predetermined energy range (the low pulse height threshold Lw to the first pulse height threshold Uw) including the expected pulse height A, which is a detection range, to be as wide as possible within a range which is four times of the half width value FWHM with the expected pulse height A as the center of the range, so as not to be affected by noise at the low pulse height side, or deformation or a pileup peak at the high pulse height side. Here, by considering that an actual target peak does not become completely symmetrical unlike a normal distribution, a lower limit of the low pulse height threshold Lw is set to expected pulse height A−half width value FWHM×2, and the low pulse height threshold Lw and the first high pulse height threshold Uw are set such that the total counting rate in the range from the low pulse height threshold Lw to the expected pulse height A is equal to the total counting rate in the range from the expected pulse height A to the first high pulse height threshold Uw. That is, it is appropriate to set the expected pulse height A to the center of gravity of the predetermined energy range Lw to Uw. In FIG. 3, in the energy spectrum in which no pileup peak appears, the low pulse height threshold Lw and the first high pulse height threshold Uw are set as: low pulse height threshold Lw=expected pulse height A−half width value FWHM×0.75, and first high pulse height threshold Uw=expected pulse height A+half width value FWHM× 0.75.

For the pulses from the input pulse multiplier 12A, it is appropriate to detect, as the pulse height of the target peak, the average pulse height obtained by averaging, by the exponential smoothing method, the pulse heights within the predetermined energy range Lw to Uw, that is, the average pulse height obtained by exponentially weighting pulse heights such that the later the pulse height is, the more the pulse height is weighted.

Figure 4:
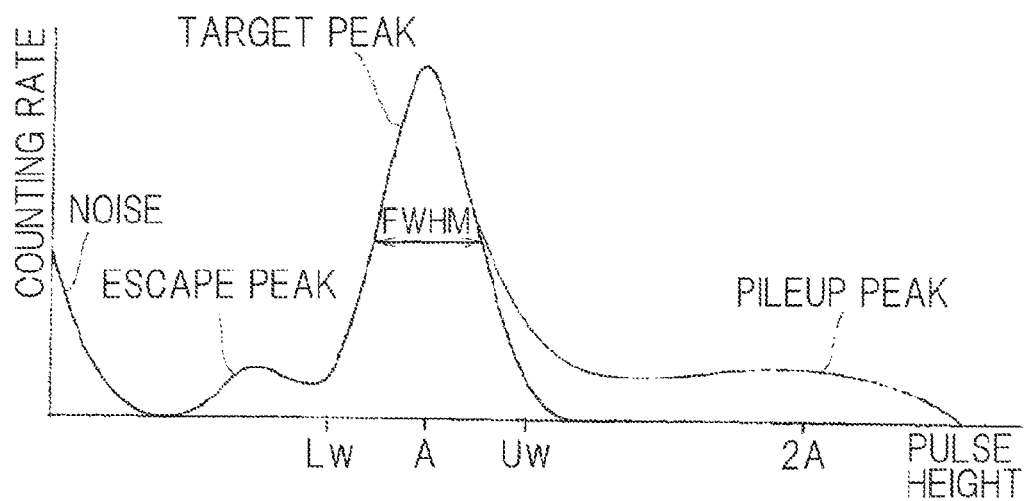
FIG. 4 illustrates other examples of the energy spectrums including their respective target peaks.

FIG. 4 shows other examples of the energy spectrums including their respective target peaks, in each of which the half value width FWHM of the target peak is narrower than that in FIG. 3 and an escape peak exists. In this case, the low pulse height threshold Lw should be set as closer to the expected pulse height A as possible so as not to be affected by an escape peak at the low pulse height side. However, considering that the target peak should be covered as much as possible within the predetermined energy range Lw to Uw, it is appropriate to set an upper limit of the low pulse height threshold Lw to be expected pulse height A−half value width FWHM×0.5. In FIG. 4, in the energy spectrum in which no pileup peak appears, the low pulse height threshold Lw and the first high pulse height threshold Uw are set as: low pulse height threshold Lw=expected pulse height A−half value width FWHM×0.9, and first high pulse height threshold Uw=expected pulse height A+half value width FWHM×0.9.

From the consideration in FIG. 3 and FIG. 4, it can be understood that the aforementioned setting of the predetermined energy range Lw to Uw including the expected pulse height A and detecting operation of the pulse height of the target peak in the second correcting unit 14A are appropriate. That is, in the second correcting unit 14A, it is appropriate that the predetermined energy range Lw to Uw is the range Lw to Uw from the low pulse height threshold Lw which is lower than the expected pulse height A by the half to two times of the half value width FWHM of the target peak, to the first high pulse height threshold Uw which is higher than the expected pulse height A, and for the X-ray energy spectrum to be analyzed, the low pulse height threshold Lw and the first high pulse height threshold Uw are set such that the total counting rate within the range from the low pulse height threshold Lw to the expected pulse height A is equal to the total counting rate within the range from the expected pulse height A to the first high pulse height threshold Uw, and for the pulses from the input pulse multiplier 12A, the average pulse height obtained by averaging, by the exponential smoothing method, pulse heights within the range Lw to Uw from the low pulse height threshold Lw to the first high pulse height threshold Uw is detected as the pulse height of the target peak.

Figure 5:
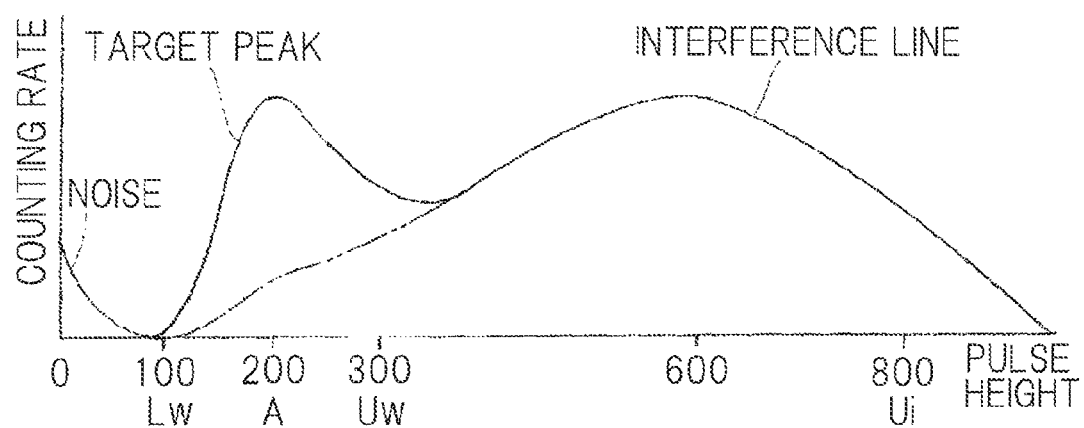
FIG. 5 illustrates still other examples of the energy spectrums including their respective target peaks.

FIG. 5 shows still other examples of the energy spectrums including their respective target peaks, in each of which interfering line exists. In FIG. 5, an energy spectrum for a case where a considerable amount of elements to be analyzed is contained is indicated by a solid line, an energy spectrum for a case where only a small amount of elements to be analyzed is contained is indicated by a two-dot chain line, and the two energy spectrums are shown in an overlapping manner. In addition, the pulse height is a channel value for a case where a multichannel analyzer having 1000 channels is used. Here, the interfering line is a tertiary line with respect to X-rays to be analyzed, and has, at a vertex of the interfering line in the spectrum, a pulse height of 600, which is third times of the expected pulse height A (200). In this case, when a counting rate at a vertex of the target peak is smaller than a value equivalent to a counting rate at the vertex of the interfering line, that is, when the energy spectrum indicated by the two-dot chain line in FIG. 5 is provided, even if the low pulse height threshold Lw and the first high pulse height threshold Uw are respectively set at 100 and 300 in order to cause the pulse height of the target peak to match the expected pulse height A through feedback control by the second correcting unit 14A, the pulse height of the target peak being detected is shifted toward the high pulse height side in which the interfering line exists, and thus the energy spectrum is entirely compressed toward the low pulse height side. As a result, the pulse height at the vertex of the interfering line matches the expected pulse height A of 200. This makes accurate analysis impossible.

Therefore, in the X-ray analyzing apparatus according to the present embodiment, in the feedback control stopping unit 16A, the low pulse height threshold Lw and the second high pulse height threshold Ui which is equal to or greater than two times of the expected pulse height A are set as described above. Here, in order to deal with interfering lines including a quartic line, the second high pulse height threshold Ui is set to 800 which is four times of the expected pulse height A (200). However, in order to prevent cosmic rays from being included in interfering lines to be coped with, it is appropriate to set the upper limit of the second high pulse height threshold Ui to be five times of the expected pulse height A, and in addition, the second high pulse height threshold Ui is set to be higher than the first high pulse height threshold Uw. In the preliminary measurement, for the pulses from the input pulse multiplier 12A, the feedback control stopping unit 16A obtains an average pulse height by averaging, by the exponential smoothing method, pulse heights within the range from the low pulse height threshold Lw to the second high pulse height threshold Ui. This average pulse height should match the pulse height of the target peak detected by the second correcting unit 14A, as described above, if the interfering line does not exist. Thus, in the preliminary measurement, when a difference between the average pulse height and the pulse height of the target peak, which is detected by the second correcting unit 14A is greater than a predetermined value, the feedback control stopping unit 16A determines that the interfering line exists. The predetermined value may be obtained in advance through an experiment.

Furthermore, when determining that the interfering line exists, the feedback control stopping unit 16A stops the second correcting unit 14A outputting the second gain, thereby to set, to the fixed value including only the first gain, the gain to be inputted to the input pulse multiplier 12A. Accordingly, even in a situation where the interfering line is mixed in the energy spectrum and the second correcting unit 14A is unable to correctly detect the pulse height of the target peak, the appropriately estimated pulse height of the target peak can be caused to match the expected pulse height A and can be stabilized, by using the first gain outputted from the first correcting unit 13A. As described above with reference to FIG. 3 to FIG. 5, the configuration of the second correcting unit 14A and the feedback control stopping unit 16A in the X-ray analyzing apparatus according to the present embodiment is appropriate.

Moreover, in the X-ray analyzing apparatus according to the present embodiment, the feedback control stopping unit 16A further has a second determination criterion for determining that the interfering line exists when a value obtained by adding the first gain to the second gain is outside a predetermined range, in the preliminary measurement. This predetermined range, within which the value obtained by adding the first gain to the second gain should fall if the interfering line does not exist, can be also obtained in advance through an experiment. For example, the range is 0.8 to 2. When it is determined that the interfering line exists on the basis of at least one of the first determination criterion and the second determination criterion, output of the second gain from the second correcting unit 14A is stopped, and thus, the gain to be inputted to the input pulse multiplier 12A is set to the fixed value including only the first gain. Accordingly, the interfering line mixed in the energy spectrum can be more reliably detected and coped with.

However, the feedback control stopping unit 16A may have only one of the first determination criterion and the second determination criterion. When the feedback control stopping unit 16A has the second determination criterion only, setting of the predetermined energy range including the expected pulse height and detecting operation of the pulse height of the target peak in the second correcting unit 14A are not limited to those described above, and various known techniques can be applied.

Furthermore, in the present invention, the criteria for the feedback control stopping unit to determine presence/absence of the interfering line are not limited to the first determination criterion and the second determination criterion, and various known techniques can be applied. In the present invention, setting of the predetermined energy range including the expected pulse height and detecting operation of the pulse height of the target peak in the second correcting unit are also not limited to those described above as long as setting and detecting operation correspond to the criteria for the feedback control stopping unit to determine presence/absence of the interfering line, and various known techniques can be applied.

An example of operations from the preliminary measurement to the main measurement in the X-ray analyzing apparatus according to the present embodiment will be described. First, the first gain G1 and the second gain G2 are set in advance to 1.0 and 0, respectively, and the first correcting unit 13A calculates and outputs, in the first 0.1 second of the preliminary measurement, an initial value G1i of the first gain G1 as the gain to cause the pulse height of the target peak estimated by obtaining the sum of counting rates, to match the predetermined expected pulse height. When the counting rate is high, the calculated first gain G1i is less than an appropriate value because the pulse height is lowered and the sum of counting rates obtained by the first correcting unit 13A is less than the actual one. Thus, in order to calculate the more realistic first gain G1, in the next 0.1 second of the preliminary measurement, the first gain G1 and the second gain G2 are set to G1i and 0, respectively, and the first correcting unit 13A again calculates and outputs a real value G1r of the first gain G1 as the gain to cause the pulse height of the target peak estimated by obtaining the sum of counting rates, to match the predetermined expected pulse height.

Further, in the last 0.1 second of the preliminary measurement, the first gain G1 is set to G1r, and the second correcting unit 14A detects the pulse height of the target peak, and calculates and outputs the second gain G2, which is the gain to be added to the first gain G1i in order to cause the detected pulse height of the target peak, to match the expected pulse height. Subsequently, presence/absence of the interfering line is determined by the feedback control stopping unit 16A, and then, the main measurement is started.

In the X-ray analyzing apparatus according to the present embodiment, after a predetermined waiting time (selected from among 0 second, four seconds, and eight seconds, for example) which corresponds to the sum of counting rates obtained by the first correcting unit 13A has elapsed since the feedback control stopping unit 16A determines that the interfering line exists in the preliminary measurement, the gain to be inputted to the input pulse multiplier 12A is set to the fixed value including only the first gain G1i, and the main measurement is started. The reason is that in order to perform accurate analysis for the main measurement using only the first gain, start of the main measurement is desired to be delayed until the pulse height of the target peak which is lowered by peak shift becomes stable, and that the length of the waiting time should be set appropriately depending on the sum of counting rates obtained by the first correcting unit 13A. However, whether or not this waiting time needs to be set in the feedback control stopping unit 16A is determined depending on accuracy desired for analysis and a time which can be taken for the analysis.

Similarly to the aforementioned pulse height stabilizer 11A corresponding to the secondary X-rays 7A, the pulse height stabilizer 11B corresponding to the secondary X-rays 7B also includes an input pulse multiplier 12B, a first correcting unit 13B, a second correcting unit 14B, a gain adder 15B, and a feedback control stopping unit 16B.

In the X-ray analyzing apparatus according to the present embodiment, the first correcting units 13A, 13B each configured to output the first gain G1 to cause the pulse height of the target peak which is estimated on the basis of the sum of counting rates obtained in the preliminary measurement, to match the predetermined expected pulse height A, and the second correcting units 14A, 14B each configured to output, in real time through feedback control, the second gain G2 to be added to the first gain G1 in order to cause the pulse height of the target peak detected within the predetermined energy range Lw to Uw to match the expected pulse height A, are provided in combination. Accordingly, even when peak shift occurs, in a considerably short time, the first gain G1 is outputted as an initial gain value and the second gain G2 is added to the first gain G1 so that feedback correction is performed. Therefore, start of the main measurement does not need to be waited (except for a case where predetermined waiting times are set in the feedback control stopping units 16A, 16B) until the pulse height of the target peak which is lowered by peak shift becomes stable. Further, even when the X-ray intensity suddenly changes, the pulse height of the target peak is not lost but can be correctly detected.

Moreover, the feedback control stopping units 16A, 16B are provided each of which is configured to appropriately determine presence/absence of the interfering line with respect to the target peak, and to set, when determining that the interfering line exists, the gain to a fixed value including only the first gain G1. Accordingly, even in a situation where the interfering line is mixed in the energy spectrum and the second correcting units 14A, 14B are unable to correctly detect the pulse height of the target peak, the appropriately estimated pulse height of the target peak is caused to match the expected pulse height A and is stabilized, by using the first gain G1 outputted from the first correcting units 13A, 13B. Therefore, even when peak shift occurs, the peak shift can be corrected speedily and appropriately, so that accurate analysis can be performed in a short time.

In the above description, the apparatus according to the present embodiment is an X-ray fluorescence spectrometer which is a wavelength dispersive type and a simultaneous multi-elements analysis type. However, an apparatus according to the present invention may be one of other X-ray analyzing apparatuses including a wavelength dispersive and scanning type X-ray fluorescence spectrometer, an energy dispersive X-ray fluorescence spectrometer, and an X-ray diffractometer. In addition, the detectors to be used may be a detector other than a gas-flow type proportional counter, for example, a sealed off proportional counter, a scintillation counter, or a semiconductor detector.

Although the present invention has been fully described in connection with the preferred embodiment thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS 7A, 7B . . . incident X-ray
8A, 8B . . . detector
9A, 9B . . . high-speed AD converter
10A, 10B . . . counting unit
11A, 11B . . . pulse height stabilizer
12A, 12B . . . input pulse multiplier
13A, 13B . . . first correcting unit
14A, 14B . . . second correcting unit
15A, 15B . . . gain adder
16A, 16B . . . feedback control stopping unit
A . . . expected pulse height
FWHW . . . half value width of target peak
Lw . . . low pulse height threshold
Uw . . . first high pulse height threshold
Ui . . . second high pulse height threshold

What is claimed is:

1. An X-ray analyzing apparatus comprising:
   a detector configured to generate a number of pulses having pulse heights corresponding to energy of incident X-rays, the number corresponding to intensity of the X-rays;
   a high-speed AD converter configured to digitalize the pulses generated by the detector;
   a pulse height stabilizer configured to stabilize, for pulses inputted from the high-speed AD converter, a pulse height of a target peak which is a peak in an X-ray energy spectrum to be analyzed; and
   a counting unit configured to obtain, for pulses from the pulse height stabilizer, a counting rate within a set pulse height range, wherein
   the pulse height stabilizer includes
      an input pulse multiplier configured to multiply the pulses inputted from the high-speed AD converter with an inputted gain, and to output the pulses,
      a first correcting unit configured to, in preliminary measurement before main measurement, obtain, for pulses from the input pulse multiplier, a sum of counting rates, to estimate the pulse height of the target peak on the basis of the obtained sum of counting rates, and to output a first gain which is a gain to cause the estimated pulse height of the target peak to match a predetermined expected pulse height, a second correcting unit configured to detect the pulse height of the target peak within a predetermined energy range including the expected pulse height on the basis of the pulses from the input pulse multiplier, and to output, in real time through feedback control, a second gain which is a gain to be added to the first gain in order to cause the detected pulse height of the target peak to match the expected pulse height, a gain adder configured to add the inputted first gain to the inputted second gain to obtain a gain, and to output the gain to the input pulse multiplier, and a feedback control stopping unit configured to determine presence/absence of an interfering line with respect to the target peak, and, when determining that the interfering line exists, to stop the second correcting unit outputting the second gain, thereby to set the gain to be inputted to the input pulse multiplier, to a fixed value including only the first gain.

2. The X-ray analyzing apparatus as claimed in claim 1, wherein
in the second correcting unit,
the predetermined energy range is a range from a low pulse height threshold which is lower than the expected pulse height by a half to two times of a half value width of the target peak, to a first high pulse height threshold which is higher than the expected pulse height, and the low pulse height threshold and the first high pulse height threshold are set such that, for the X-ray energy spectrum to be analyzed, a total counting rate within a range from the low pulse height threshold to the expected pulse height is equal to a total counting rate within a range from the expected pulse height to the first high pulse height threshold, for the pulses from the input pulse multiplier, an average pulse height obtained by averaging, by an exponential smoothing method, pulse heights within the range from the low pulse height threshold to the first high pulse height threshold is detected as the pulse height of the target peak, and in the feedback control stopping unit,
the low pulse height threshold and a second high pulse height threshold, which is equal to or greater than two times of the expected pulse height are set, and
in the preliminary measurement, for the pulses from the input pulse multiplier, when a difference between the pulse height of the target peak detected by the second correcting unit and an average pulse height obtained by averaging, by the exponential smoothing method, pulse heights within a range from the low pulse height threshold to the second high pulse height threshold is greater than a predetermined value, it is determined that the interfering line exists.

3. The X-ray analyzing apparatus as claimed in claim 1, wherein
in the preliminary measurement, when a value obtained by adding the first gain to the second gain is outside a predetermined range, the feedback control stopping unit determines that the interfering line exists.

4. The X-ray analyzing apparatus as claimed in claim 1, wherein, after a predetermined waiting time corresponding to the sum of counting rates obtained by the first correcting unit has elapsed since the feedback control stopping unit determines in the preliminary measurement that the interfering line exists, the feedback control stopping unit sets a gain to be inputted to the input pulse multiplier, to the fixed value including only the first gain, and the main measurement is started.

* * * * *